(12) United States Patent
Ezzat et al.

(10) Patent No.: US 10,167,719 B2
(45) Date of Patent: Jan. 1, 2019

(54) METHODS AND SYSTEMS FOR EVALUATION OF ROCK PERMEABILITY, POROSITY, AND FLUID COMPOSITION

(71) Applicant: Halliburton Energy Services, Inc., Houston, TX (US)

(72) Inventors: Abdalla Moustafa Ezzat, Houston, TX (US); Michael T. Pelletier, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/404,186

(22) PCT Filed: Sep. 3, 2013

(86) PCT No.: PCT/US2013/057825
§ 371 (c)(1),
(2) Date: Nov. 26, 2014

(87) PCT Pub. No.: WO2015/034463
PCT Pub. Date: Mar. 12, 2015

(65) Prior Publication Data
US 2015/0354352 A1    Dec. 10, 2015

(51) Int. Cl.
*E21B 49/02* (2006.01)
*G01N 33/24* (2006.01)
*G01N 15/08* (2006.01)

(52) U.S. Cl.
CPC ......... *E21B 49/02* (2013.01); *G01N 15/0826* (2013.01); *G01N 33/24* (2013.01)

(58) Field of Classification Search
CPC ..................................................... E21B 49/02
(Continued)

(56) References Cited

U.S. PATENT DOCUMENTS 2,379,045 A * 6/1945 Sturgis ................. E21B 49/005
203/41
3,018,660 A * 1/1962 Schmid ................ G01N 15/082
73/152.09

(Continued)

FOREIGN PATENT DOCUMENTS

WO     WO 2012017197 A1 *  2/2012   ............. E21B 43/20

OTHER PUBLICATIONS

Author: Jyun-Syung Tsau, Title: Near Miscible CO2 Application to Improve Oil Recovery for Small Producers, Date: Oct. 29, 2010, Publisher: Research Partnership to Secure Energy for America, RPSEA Final Report 07123-03.FINAL. pp. 66.*

(Continued)

*Primary Examiner* — Lisa Caputo
*Assistant Examiner* — Roger Hernandez-Prewit
(74) *Attorney, Agent, or Firm* — Tenley Krueger; Baker Botts L.L.P.

(57) ABSTRACT

Methods and systems for substantially simultaneous evaluation of rock sample permeability and porosity, and composition of formation fluids, are provided. Such methods and systems may be used to evaluate the permeability, porosity, and composition of at least a portion of a subterranean formation in a drilling operation. An example of such a method may include passing a cleaning fluid through the rock sample so as to extract at least a portion of one or more formation fluids from the rock sample in an effluent comprising the cleaning fluid and the portion of the one or more formation fluids; and determining one or more properties of the effluent so as to determine the composition of the portion of the one or more formation fluids, and so as to determine the permeability and porosity of the rock sample.

18 Claims, 2 Drawing Sheets

(58) Field of Classification Search
USPC .............. 73/152.05, 152.39, 152.41, 152.07
See application file for complete search history.

(56) References Cited

U.S. PATENT DOCUMENTS

| | | | | |
|---|---|---|---|---|
| 3,140,599 | A | * | 7/1964 | Rahme ................ G01N 15/0826 73/38 |
| 3,474,864 | A | * | 10/1969 | Hurd ....................... C09K 8/584 166/272.3 |
| 4,722,095 | A | | 1/1988 | Muegge et al. |
| 4,868,751 | A | | 9/1989 | Dogru et al. |
| 5,079,948 | A | | 1/1992 | Collins et al. |
| 7,081,615 | B2 | | 7/2006 | Betancourt et al. |
| 7,392,138 | B2 | | 6/2008 | Frechin et al. |
| 7,989,401 | B2 | * | 8/2011 | Kurian et al. ....... C09K 8/5083 166/295 |
| 2008/0216559 | A1 | | 9/2008 | Hilab |
| 2012/0199355 | A1 | * | 8/2012 | Boluk ..................... E21B 43/20 166/305.1 |
| 2012/0223235 | A1 | | 9/2012 | Maucec |

OTHER PUBLICATIONS

Authors: K. Visscher and P. F. Mijnlieff, Title: Temperature and concentration dependent viscosity and gelation temperature of ABA triblock copolymer solutions, Date: 1991, Publication: Rheol Acta, vol. 30, pp. 559-574.*

International Search Report and Written Opinion issued in related PCT Application No. PCT/US2013/057825 dated May 23, 2014, 10 pages.

International Preliminary Report on Patentability issued in related PCT Application No. PCT/US2013/057825 dated Mar. 8, 2016 (7 pages).

* cited by examiner

METHODS AND SYSTEMS FOR EVALUATION OF ROCK PERMEABILITY, POROSITY, AND FLUID COMPOSITION

CROSS-REFERENCE TO RELATED APPLICATION

This application is a U.S. National Stage Application of International Application No. PCT/US2013/057825 filed Sep. 3, 2013, which is hereby incorporated by reference in its entirety.

BACKGROUND

Hydrocarbons, such as oil and gas, are commonly obtained from subterranean formations. The development of subterranean operations and the processes involved in removing hydrocarbons from a subterranean formation are complex. Typically, subterranean operations involve a number of different steps such as, for example, drilling the wellbore at a desired well site, treating the wellbore to optimize production of hydrocarbons, and performing the necessary steps to produce and process the hydrocarbons from the subterranean formation.

Modern oil field operations generally involve monitoring one or more parameters and conditions encountered downhole, including petrophysical properties such as the porosity and permeability of the rock comprising the formation, or the composition of fluids in the formation (e.g., formation fluids and components of formation fluids). Porosity may indicate, for example, the volume of oil or gas that may be present in the formation as a whole, while permeability may be used to assess the relative ease with which formation fluids (such as oil and gas within the formation) will flow into the well, that is, the productivity of the well.

Thus, during or after drilling, reservoirs are often evaluated to determine various properties of the formation and the hydrocarbons contained therein. These characteristics of a formation may be extrapolated from a small portion of the formation exposed during the drilling process. For example, data may be collected during drilling, well testing, logging, and coring operations. In many cases, rock samples from the formation (such as core samples or cuttings) may be the source of such data.

This information about the formation may be helpful in optimizing drilling operations (e.g., whether stimulation such as fracturing or acidization is necessary), assessing the well's productivity based upon permeability measurements, or other analyses. Because this information often impacts the operation of the well drilling process, it may be desirable to determine the formation information as quickly and efficiently as possible.

Conventional methods and equipment for assessing parameters such as fluid characterization, porosity, and permeability analyze each of those parameters using separate analytical processes. For example, a rock sample may be obtained, and all formation fluid may be washed from the sample and collected for characterization or other analysis. Then, separately, another fluid may be passed through the rock sample so as to obtain measurements of flow rate and/or pressure difference of the fluid passed over the rock sample (using, e.g., core flood equipment, permeability-measurement devices, and various other equipment). Also separately, porosity of the rock sample may be assessed by a conventional process and equipment, such as gas porosimeters (a helium/argon/carbon dioxide/nitrogen, or krypton), mercury injection, brine saturation, and pressure-transient plus decay methods, each of which include means of estimating total volume and pore volume of the sample. In some instances, accurate permeability and/or porosity measurements specific to hydrocarbons within the formation fluid may only be possible by rehabilitating the rock sample—that is, re-saturating it with natural or simulated formation water prior to running porosity and/or permeability tests, so as to accurately capture the effect of the formation water upon oil phase permeability and relative porosity. Consequently, operators may be forced to delay operations while these different analyses are taking place, which may cause various operational delays and added expenditures during the drilling process.

FIGURES

Some specific exemplary embodiments of the disclosure may be understood by referring, in part, to the following description and the accompanying drawings.

The features and advantages of the present disclosure will be readily apparent to those skilled in the art. While numerous changes may be made by those skilled in the art, such changes are within the spirit of the invention.

DETAILED DESCRIPTION

The present disclosure relates to systems and methods for evaluating permeability, porosity, and composition of fluids of rocks. More particularly, the present disclosure relates to systems and methods for the substantially simultaneous evaluation of permeability, porosity, and the composition of fluids found in rock samples, for example, from subterranean formations.

As used herein, the term "substantially simultaneous" means taking place during the course of a single, substantially unified procedure. The term "substantially simultaneous" does not imply, by itself, that certain actions must be undertaken or otherwise take place at the same or at substantially the same point of time. In some embodiments, actions may take place over the course of a period of time such as one, two, or more hours, or some other reasonable time necessary for the measurements and techniques discussed herein.

In some embodiments, the present disclosure provides a method that includes: passing a cleaning fluid at a flow rate through a rock sample at a differential pressure, so as to extract at least a portion of one or more formation fluids from the rock sample; collecting an effluent comprising the cleaning fluid and the portion of the one or more formation fluids; determining one or more properties of the effluent; determining the volume of the rock sample and the volume of the portion of the one or more formation fluids; based at least in part on one or more of the properties of the effluent, determining one or more properties of the portion of the one or more formation fluids; based at least in part on one or more of (i) one or more properties of the effluent, (ii) the flow rate of the cleaning fluid, and (iii) the differential pressure of the cleaning fluid, determining a permeability value of the rock sample; and based at least in part on one or more of (i) the volume of the portion of the one or more formation fluids and (ii) the volume of the rock sample, determining a porosity value of the rock sample.

In some embodiments, the present disclosure provides a method that includes: passing a first cleaning fluid at a first flow rate through a rock sample at a first differential pressure, so as to extract at least a first portion of one or more formation fluids from the rock sample; collecting a first effluent comprising the first cleaning fluid and the first portion of the one or more formation fluids; passing a second cleaning fluid at a second flow rate through the rock sample at a second differential pressure, so as to extract at least a second portion of the one or more formation fluids from the rock sample; collecting a second effluent comprising the second cleaning fluid and the second portion of the one or more formation fluids; determining one or more properties of each of the first effluent and the second effluent; determining the volume of the rock sample, the volume of the first portion of the one or more formation fluids, and the volume of the second portion of the one or more formation fluids; based at least in part on one or more of the properties of the first effluent, determining one or more properties of the first portion of the one or more formation fluids; based at least in part on one or more of the properties of the second effluent, determining one or more properties of the second portion of the one or more formation fluids; based at least in part on one or more of (i) one or more of the properties of the first effluent, (ii) the first flow rate of the first cleaning fluid, and (iii) the first differential pressure of the first cleaning fluid, determining a first permeability value of the rock sample; and based at least in part on one or more of (i) the volume of the first portion of the one or more formation fluids, (ii) the volume of the second portion of the one or more formation fluids, and (ii) the volume of the rock sample, determining a porosity value of the rock sample.

In some embodiments, the present disclosure provides a system that includes: a fluid processing unit that removes one or more rock samples from a drilling fluid that has been circulated in a well bore penetrating at least a portion of a subterranean formation; and a rock sample analysis system configured to pass a cleaning fluid through one of the one or more rock samples at a flow rate and a differential pressure so that the cleaning fluid extracts at least a portion of one or more formation fluids from the one of the one or more rock samples in an effluent comprising the cleaning fluid and the portion of the one or more formation fluids, the rock sample analysis system comprising equipment configured to obtain one or more rock sample analysis measurements selected from the group consisting of: the flow rate of the cleaning fluid, the differential pressure of the cleaning fluid, one or more properties of the cleaning fluid, one or more properties of the effluent, and the effluent's mass.

In certain embodiments, the evaluation systems and methods of the present disclosure may be more efficient than conventional techniques, thereby allowing more up-to-date analysis of the formation during drilling production. For example, in certain embodiments, the embedded fluid of the formation may be taken from the rock sample itself for analysis; this may provide a more accurate characterization of the formation fluids than conventional techniques that rely upon analysis of the drilling mud, and characterization of the formation based upon the hydrocarbons present in the drilling mud. In some embodiments, the process of cleaning formation fluids from the rock sample may be combined in whole or in part with the assessment of the sample's permeability and/or porosity, which may save substantial time over traditional laboratory analysis techniques, in some cases as much as 10 days. Some methods may be sufficiently flexible to balance speed and accuracy of measurements.

The present disclosure in some embodiments may provide a procedure that allows the near-simultaneous evaluation of permeability, porosity, and formation fluid characterization of a rock sample according to a generalized process including: passing a cleaning fluid of known and/or determined properties through the rock sample at a set flow rate and/or differential pressure so as to extract at least a portion of one or more formation fluids within the rock sample; collecting an effluent comprising the cleaning fluid and extracted formation fluid(s) and analyzing the effluent so as to determine one or more properties of the formation fluid(s); determining the volumes of the rock sample and formation fluid(s); and determining permeability and porosity values of the rock sample. The process of some embodiments allows for a substantial degree of flexibility in many regards. For example, some embodiments allow for flexibility in the kinds of measurements obtained (e.g., effective oil phase permeability, effective water phase permeability, or absolute permeability, one or all of which may be obtained based at least in part upon the phase—e.g., degree of hydrophilicity or hydrophobicity—of cleaning fluid). Furthermore, the general process may be repeated one, two, three, or more times. Repetition may involve minimal, if any, modifications to the process and/or equipment, and may provide more accurate and/or different in kind measurements (although at the potential expense of greater time expenditure); for example, repetition in some embodiments may include use of a different cleaning fluid with little or no other modification to the process. The methods of some embodiments therefore may balance the desired speed and accuracy of rock sample analysis as part of the drilling process. Other modifications to improve accuracy may include, but are not limited to, additional soaking of the rock sample in the cleaning fluid, and/or heating the rock sample (e.g., to increase extracted formation fluid and/or to simulate downhole conditions).

The rock sample may be obtained by any conventional means as employed before, during, or after the drilling process (e.g., sidewall coring such as percussion and/or rotary sidewall coring, or extraction of cuttings during drilling). It may vary in size (that is, mass and/or volume). In some embodiments, the rock samples may comprise a sidewall core of 0.5 to 2.5 inches in diameter, or in other embodiments the core sample may be 2.5 to 6 inches in diameter. Length may vary from inches to dozens of feet (e.g., 60 feet or more), and mass may vary from approximately 5 to 50 g. However, it should be recognized that any size rock sample could be used in the systems and methods of the present disclosure. In some embodiments, the downhole depth from which the rock sample originated may be determined so as to pinpoint the location of a formation to which information determined from that rock sample corresponds. For example, tracer stamping of cuttings and/or lag time measurements may be made so as to associate a cutting with a specific travel time up the well and/or depth in the well.

As previously noted, the process of some embodiments may include passing one or more cleaning fluids through a rock sample. The cleaning fluid of some embodiments may include a solvent suitable for extracting all or a portion of the formation fluids in the rock sample. Formation fluids of some rock samples may include dual phase liquids and/or gases (e.g., liquids and/or gases containing both a hydrocarbon fraction—which may include oil, gas, and other hydrocarbons—and a water phase fraction including non-hydrocarbon materials such as water and other non-hydrocarbon compounds in the formation, which may be referred to generally as "formation water"). Thus, a suitable solvent for extracting the hydrocarbon fraction of the formation fluids may be a hydrophobic or oleophilic (e.g., oil-phase) solvent. Such solvents may include, but are not limited to, benzene, toluene, and xylene. Any oil-phase solvent may be suitable, although some solvents may be preferable to others due to adverse side effects. For example, pentane or butane may result in asphalt precipitation when contacting a hydrocarbon fraction of formation fluids, which may adhere to pores within the rock sample and corrupt the accuracy of measurements obtained relating to porosity and permeability. In general, other suitable oil-phase solvents may include any one or more of: aliphatic hydrocarbons such as hexane, aromatic solvents (such as toluene, as already mentioned), glycol ether solvents such as 2-butoxyethanol (sometimes referred to by the Dow Chemical Company brand name BUTYL CELLOSOLVE™); or other organic solvents in general (some further examples of which may include benzene-methylalcohol; carbon tetrachloride; chloroform; ethylene dichloride; napththa; tetrachloroethylene; and trichloroethylene).

On the other hand, hydrophilic solvents (e.g., water, glycol, methanol) may also or instead be used as the cleaning fluid, with the realization that such solvents will tend to extract formation water rather than the hydrocarbon fraction. In some embodiments, the cleaning fluid may comprise amphiphilic solvents or additives giving the cleaning fluid amphiphilic properties (e.g., surfactants, such as acetone or other ketone surfactants) so as to extract at least a portion of both the hydrocarbon fraction and the formation water. Thus, in some embodiments, the phase of the cleaning fluid may be selected so as to target a desired portion of the formation fluid(s) to extract from the rock sample.

Furthermore, in some embodiments, the cleaning fluid may be substantially in the gas state, while in other embodiments it may be substantially a liquid state. It may be in two-phase flow (e.g., both liquid and gas state). In addition to the aforementioned possible cleaning fluids, a gaseous cleaning fluid of some embodiments may be carbon dioxide, nitrogen, and/or air.

In addition, either or both of the cleaning fluid's phase (e.g., hydrophobic, hydrophilic, amphiphilic) and its state (gas, liquid, two-phase) may affect the permeability and/or porosity values obtained from measurements of the process of various embodiments, as discussed in greater detail elsewhere in this disclosure.

The cleaning fluid may be passed through the rock sample at a first flow rate and first differential pressure. In some embodiments, one of these is fixed. For example, the fluid may be driven at constant flow rate, and differential pressure over the rock sample (e.g., pressure drop in fluid flow over the rock sample) may be measured. In other embodiments, the cleaning fluid may be driven such that differential pressure over the rock sample remains constant by varying flow rate of the cleaning fluid, and flow rate may be measured. Passing the cleaning fluid through the rock sample at a first flow rate and first differential pressure may in some embodiments include passing the cleaning fluid through the rock at steady state flow for at least a period of time (e.g., such that differential pressure and/or flow rate measurements are obtained at steady state conditions). In yet other embodiments, passing the cleaning fluid through the rock sample may include passing the cleaning fluid through the rock sample in one or more pulses (e.g., conducting a pulse test). Using this methodology, the rock sample may be subjected to an average pressure, and a reservoir of known volume at a higher (or lower) pressure is opened. The change in pressure is measured as the cleaning fluid flows into the rock sample from the reservoir, or out of the rock sample into the reservoir (depending upon whether a higher or lower reservoir pressure, respectively, is used). Whichever methodology is used in a particular embodiment, the flow rate and differential pressure (known and/or measured, accordingly) may in some such embodiments be used in calculating permeability of the rock sample, as discussed in greater detail elsewhere in this disclosure.

Furthermore, in some embodiments, regardless of the phase of the cleaning fluid, it may be passed through the rock sample at sufficient differential pressure and/or flow rate to extract an opposite phase portion of formation fluid. For example, with sufficiently high differential pressure, even a hydrophobic solvent may extract at least a portion of formation water from the rock sample by physical transport means. Cleaning fluid drive pressures may range from, in some embodiments, 10 to 100, 200, 500, or 1000 psi, or any pressure range within those pressures. In some embodiments, the liquid solvent drive pressure may be as low as 5 psi or as high as 1,500 psi. However, depending upon the type of rock sample (e.g., clay, oil sand, shale, etc.), a threshold differential pressure may exist beyond which the cleaning fluid should not be passed through the rock. Otherwise, the cleaning fluid may physically erode a portion of the rock sample itself, thereby corrupting the sample and adversely impacting the accuracy of permeability and/or porosity determined from the sample. Thus, some methods may further comprise determining a differential pressure at which to pass the cleaning fluid through the rock sample based at least in part upon the kind of formation from which the rock sample is obtained. A person of ordinary skill in the art with the benefit of this disclosure will recognize how to determine these threshold differential pressures for different types of rock.

The methods of some embodiments may further include determining one or more properties of the effluent (e.g., density, viscosity, composition), which may be sufficient to enable determination of permeability and/or porosity. For example, where density and/or viscosity are included in the determined one or more properties of the effluent, permeability may be determined based at least in part upon such properties of the effluent (that is, the cleaning fluid combined with the extracted formation fluid(s)) flowing through the rock sample, in recognition that the fluid flowing through the rock sample may be composed of both the cleaning liquid and extracted formation fluid(s) (and therefore the relevant properties for determining permeability and/or porosity may be those of the effluent rather than just the cleaning fluid alone). In some embodiments, the one or more properties of the effluent may be determined instrumentally (e.g., by way of a viscometer and/or densitometer through which the effluent is passed). In other embodiments, the one or more properties of the effluent may be determined analytically (e.g., based at least in part upon the composition of the effluent and one or more properties of the cleaning fluid). For instance, the mass fraction of cleaning fluid in the effluent (determination of which is discussed in greater detail below) may be used as a weighting factor in conjunction with the one or more properties of the cleaning fluid so as to extrapolate to approximate associated properties of the effluent. As a simplified example, an effluent with 90% by mass cleaning fluid may be approximated as having a viscosity equal to the viscosity of the cleaning fluid multiplied by a factor equal to the inverse of the cleaning fluid's mass fraction (1/0.9). Other similar and/or more complicated extrapolation or other calculation will be apparent to one of ordinary skill in the art with the benefit of this disclosure.

Thus, the methods of some embodiments may further include determining one or more properties of the cleaning fluid, such properties for example including but not limited to any one or more of the cleaning fluid's composition, its density and/or viscosity at operating conditions (e.g., temperature, pressure, flow rate), and any other desired property or properties. Such determinations may be made by any suitable means, including reference to known values (e.g., reference tables) or conventional measurement (e.g., viscometer). Measurement may be performed on-line (that is, part of the cleaning fluid's flow path into and through the rock sample). In some embodiments, the one or more properties of the cleaning fluid should be determined prior to passing the cleaning fluid through the rock sample so as to obtain such properties prior to extraction of formation fluid(s).

Collecting Effluent and Characterizing Formation Fluids

As previously noted, the process of some embodiments may further include collecting the effluent and determining one or more properties of the extracted formation fluid(s). For example, such one or more properties may include the composition of the extracted formation fluid(s) (e.g., characterizing the extracted formation fluid(s)).

The collected effluent may comprise the fluid stream leaving the rock sample. It may include the cleaning fluid and the extracted portion of the formation fluid(s). Methods of some embodiments may further include determining the effluent's composition. This may, in turn, include determining any one or more of the identity and amount of each compound in the effluent. Effluent composition may be determined in various embodiments by analytical and/or instrumental means. For example, the collected effluent may be weighed so as to determine its total mass; the mass fractions of extracted formation fluid and cleaning fluid, respectively, in the effluent may be determined from a simple mass balance as compared to a known mass of cleaning fluid passed through the rock sample. Alternatively or in addition, the effluent may be characterized by instrumental analysis (e.g., gas and/or liquid chromatography, mass spectrometry, etc.). Based at least in part upon any one or more of the aforementioned characterization methods, and comparison with the known and/or determined composition of the cleaning fluid, the formation fluid(s) in the effluent may be characterized. Any one or more other properties of the formation fluid (e.g., viscosity, density, etc.) may be determined based at least in part upon the one or more properties of the effluent determined according to some embodiments, and/or based at least in part upon the one or more properties of the cleaning fluid determined according to some embodiments.

The process of some embodiments may further comprise determining the volume of the rock sample and determining the volume of the formation fluid(s). The volume of the rock sample may be determined by conventional means. For example, volumetric displacement of a strongly non-wetting fluid may be used to measure bulk volume of the rock sample (i.e., the volume of the rock sample including pore volume within the sample) by submersion in a bath according to Archimedes' principle. In some instances, the non-wetting fluid may be mercury. In other instances, the rock sample may be saturated by a liquid (e.g., brine, refined oil, or toluene) and then weighed by the same means. In some embodiments, the rock sample's volume may be determined in whole or in part by measuring volume in a rock sample chamber into which cleaning fluid is passed into and through the rock sample. As one example, in processes according to some embodiments that include soaking the rock sample in a cleaning fluid, the rock sample may be removed at the end of the soaking, and volume of the cleaning fluid in the rock sample chamber after removal of the rock sample compared to volume of the cleaning fluid in the rock sample chamber with the rock sample in the chamber. In some instances, a volume so determined may correspond to the volume of the rock sample not including the pore volume within the rock sample.

The volume of the formation fluid may in certain embodiments be determined analytically. For example, the volume of the formation fluid may be determined based at least in part upon the determined composition of the effluent and/or the known or determined properties of the cleaning fluid. The volume of the formation fluid in such instances may correspond to the volume of extracted formation fluid(s) in the effluent. Moreover, where primarily only one fraction of the formation fluids is extracted, the volume of formation fluid determined may be a partial volume, that is, a volume of the extracted fraction. For example, with extraction of primarily a hydrocarbon fraction of the formation fluid by use of a hydrophobic and/or oleophilic solvent, the volume of formation fluid determined may correspond to a hydrocarbon fraction volume. Any one or more of the rock sample and formation fluid volume may be used in determining porosity (e.g., pore volume as a fraction of total volume in the rock sample), as is discussed in greater detail below.

Processes according to some embodiments may further comprise determining permeability and determining porosity.

In some embodiments, permeability may be determined (e.g., calculated, computed, measured, or otherwise deduced) based at least in part upon the determined or known properties of the cleaning fluid, the flow rate and/or differential pressure at which the cleaning fluid was passed through the rock sample, and the determined composition of the first effluent. For example, it may be calculated according to a model or equation based at least in part upon any one or more of Navier-Stokes, Poiseuille, and Darcy's Law relationships. A simplified example of a Darcy's Law relationship may take the form:

$$Q = A\left(\frac{k}{\mu}\right)\left(\frac{\Delta P}{L}\right) \qquad \text{(Eqn. 1)}$$

In Equation (1), Q is the volumetric flow rate (e.g., cm$^3$/s) of the cleaning fluid through the rock sample; $\Delta P$ is the differential pressure (e.g., dynes/cm$^2$); $\mu$ is the dynamic viscosity (e.g., poise) of the cleaning fluid; L is the length of the rock sample through which the cleaning fluid is driven (in, e.g., cm); k is the permeability of the rock sample (in, e.g., darcy), and A is the cross-sectional area of the sample facing the cleaning fluid (cm$^2$). It will be appreciated by one of skill in the art that any units of measurement can be used for these values, so long as dimensional analysis reveals internal consistency. Solving the general Darcy's law equation for k yields the sample's permeability.

Of course, other models, including more complicated models, as known in the art may be used in order to allow determination of permeability based at least in part upon the known, measured, or otherwise determined flow rate, differential pressure, and viscosity. For example, an extended Darcy's law model for multi-phase flow may be used to determine effective permeability values (e.g., a fraction of absolute permeability to which the permeability of a single phase flowing through the rock sample's pores may be attributed). As another example, experimental-based and other models that account for interactions between fluid phases may be used. One of ordinary skill in the art with the benefit of this disclosure will recognize an appropriate model of permeability in porous media to use in determining permeability values with the data and information gleaned from the processes of various embodiments of the present disclosure.

Thus, a determined permeability may be an effective oil-phase permeability (e.g., the fraction of absolute permeability attributable to oil-phase flow as opposed to water-phase flow through the porous rock sample). For example, where the extracted portion of formation fluid comprises primarily hydrocarbon fraction, the permeability so determined in association with extraction of that portion of formation fluid may be characterized as the oil phase effective permeability. Furthermore, where subsequent extraction of a formation water portion of the formation fluid (e.g., by use of a hydrophilic cleaning fluid) results in significantly higher determined permeability, one may be able to characterize much of the resistance to hydrocarbon flow in the rock sample as being due to formation water as opposed to the structure of the rock itself (e.g., the interconnectedness of pores).

Similarly, a determined permeability may be an absolute permeability. For example, absolute permeability may be determined where amphiphilic cleaning fluid is used to extract formation fluid(s); or where hydrophobic solvent is passed through the rock sample at sufficiently high differential pressure so as to extract (e.g., by physically transporting) formation water in addition to extracting hydrocarbon fraction; or where any other suitable means (e.g., high-viscosity cleaning fluid) are used to pass the cleaning fluid through the rock sample so as to remove a substantial portion of the formation fluid(s) from multiple phases. Given an effective oil-phase permeability value and an absolute permeability value, the water-phase effective permeability can then be determined analytically without the need for further pass-through, although further pass-through and/or instrumental determination may also or instead be used. The process in some embodiments may of course be reversed (e.g., water-phase effective permeability determined; absolute permeability may be determined; and then oil-phase effective permeability determined analytically). Accordingly, then, while a permeability value may be determined based at least in part upon differential pressure, flow rate, and one or more properties of the cleaning fluid, a permeability value in some embodiments may be determined based further at least in part upon the phase of the cleaning fluid passed through the rock sample.

In some embodiments, permeability may be multi-directional (e.g., in anisotropic media). In such cases, Darcy's Law or like modeling may be used in each direction to construct a permeability tensor or other multi-dimensional permeability model from which permeability may be determined (again, based at least in part upon flow rate, differential pressure, and one or more known or determined properties of the cleaning fluid). In some embodiments, the cleaning fluid may be passed through the rock in multiple passes, with each pass in a substantially different axial direction (e.g., using each of an x-axis, y-axis, and z-axis pass-through).

Furthermore, just as permeability may be multi-phase in the sense of oil or water-phase flow, it may also be multi-phase in the sense of states (e.g., gas versus liquid state flow). In some instances, permeability of porous media such as the rock sample may be different for gaseous than for liquid flow. Thus, the permeability may be determined further based at least in part upon the state of the cleaning fluid passed through the rock sample. For example, some rock samples, such as low-permeability rock samples, may exhibit different (e.g., higher) permeability for gases, which may not adhere to pore walls within the rock sample to the same degree a liquid would. In such cases, known correction factors (e.g., Klinkenberg correction, Knudsen correction, etc.) may be used to determine a liquid permeability value where a gaseous cleaning fluid is used in determination of permeability.

In some embodiments, a permeability value may be determined based further at least in part upon the type of formation from which the rock sample was obtained (e.g., shale, oil sand, sandstone, etc.). The general shape and/or interconnectedness of pores within the rock sample may be known, referenced, or derived based upon the type of formation, and this generalized pore data may then be used in determining an effective or absolute permeability.

In some embodiments, porosity may be determined (e.g., calculated, computed, measured, or otherwise deduced) based at least in part upon the volume of the effluent collected, and the volume of the rock sample. As noted previously, the volume of the effluent collected may in turn be determined based at least in part upon the determined composition of the effluent.

The porosity of the rock sample may be a pore fraction or percentage (that is, the pore volume divided by bulk volume of the rock sample). Pore volume may be determined based at least in part on the determined volume of the extracted formation fluid(s), which may have occupied the pores of the rock sample prior to extraction. Thus, in some embodiments, the greater the total portion of formation fluid(s) extracted from the sample and used in determining volume, the more accurate the porosity determination may be. Formation fluid(s) extraction may in some embodiments be increased by use of multiple pass-throughs of cleaning fluid or fluids, discussed in greater detail below. In addition, porosity may be determined further based at least in part upon the determined permeability. This may in some embodiments enable further characterization of porosity, for example, by enabling determination of the connectedness of pores in the rock sample.

Some embodiments may further include multiple passes in accordance with the various methods and features described above. That is, the process of some embodiments may further include passing a second cleaning fluid through the rock sample so as to extract a second portion of formation fluid(s); collecting a second effluent comprising the second cleaning fluid and the second portion of formation fluid(s); and characterizing the second portion of formation fluid(s). The second cleaning fluid may have the same composition as the first cleaning fluid (e.g., both the first and second cleaning fluid may be toluene, or air, or any other suitable cleaning fluid), although it may in some embodiments be different. For example, where the first cleaning fluid is hydrophobic, the second cleaning fluid may be selected so as to be hydrophilic, or in some embodiments, amphiphilic, thereby potentially enabling extraction of a different portion (e.g., part or all of a different fraction) of the formation fluid(s). Similarly, the second cleaning fluid may have the same or a different state from the first cleaning fluid, in various embodiments. Thus, the second cleaning fluid may be of like composition but different state, or of different composition and different state. Thus, for example, the methods of some embodiments may further include passing a gaseous cleaning fluid through the rock sample after passing the liquid cleaning fluid through the rock sample.

As with the first pass-through, second and successive pass-throughs may each include collecting respective second and successive (e.g., third, fourth, etc.) effluents and making similar determinations as those associated with the first pass-through. Thus, the process of some embodiments may further comprise: characterizing respective second and successive portions of the formation fluid(s) (e.g., the portion extracted in each pass-through); determining respective second and successive permeability values; and determining respective second and successive porosity values.

The effluent from each successive repeated pass-through may be collected separately, and the composition of each successive effluent may be compared with each associated permeability and/or porosity value so as to create a profile of permeability and/or porosity versus formation fluid composition. For example, where a second effluent includes a second portion of formation fluid of a particular composition (e.g., 60% hydrocarbon fraction and 40% formation water fraction), the permeability and/or porosity as to formation fluids of approximately 60/40 hydrocarbon:formation water composition may be determined, and so on for a third effluent including a third portion of formation fluid of a different composition (e.g., 50%, 50%).

In some embodiments, the permeability and/or porosity values resulting from multiple pass-throughs may be used in determining other, combined, permeability and/or porosity values. For instance, as previously referenced, a second permeability value determined following a single pass-through of cleaning fluid may be an effective permeability of a single phase, and a subsequent permeability may be an absolute permeability; an effective permeability of another phase may then be determined based at least in part upon the two previously-determined permeability values.

Furthermore, the processes of some embodiments, may further comprise soaking the rock sample in some additional portion of cleaning fluid after passing the cleaning fluid through the rock sample at the flow rate and/or differential pressure used in determining permeability. Such soaking may increase the amount of formation fluid(s) extracted in the cleaning fluid, and could thereby yield more accurate porosity calculations (e.g., virtue of the greater proportion of formation fluid(s) removed into the effluent). Soaking in some embodiments may take place for a period of time ranging from about 1 minute to about 2 hours. In other embodiments, soaking may take place from about 1 minute to about 30 minutes; from about 5 minutes to about 25 minutes; or from about 10 minutes to about 20 minutes. After soaking, the additional cleaning fluid and additional extracted formation fluid(s) may form an additional effluent, which may be collected with the effluent from the previous pass-through of the cleaning fluid, and the formation fluid volume may be determined based at least in part upon the total effluent collected (e.g., the effluent from the pass-through step and the additional effluent collected after soaking). Further pass-through (e.g., of a second cleaning fluid) may follow this soaking step, which may in turn be followed by additional soaking, such that the process of some embodiments may include passing a first cleaning fluid through the rock sample; soaking the rock sample in additional first cleaning fluid; passing a second cleaning fluid through the rock sample; soaking the rock sample in additional second cleaning fluid; and so on, as may be required or desired in connection with any particular analysis of the rock sample.

In addition, the process of some embodiments may further comprise heating the rock sample. Heating may be accomplished by, for example, steaming the rock sample directly, or by steaming, heating coils, or other means for heat exchange with a chamber holding the rock sample and in which the cleaning fluid is passed through the rock. Heating may take place while the cleaning fluid is passed through the rock sample, or it may take place while the rock sample is soaked in additional cleaning fluid. Heating may increase the amount of formation fluid(s) extracted from the rock sample, and/or it may help simulate downhole conditions so as to provide for more accurate determinations of, e.g., permeability and/or porosity. Similarly, a chamber or other vessel holding the rock sample may be pressurized so as to simulate downhole conditions.

Equipment

Any equipment capable of passing one or more cleaning fluids through a rock sample may be suitable for various processes described herein. Such equipment may further include devices for obtaining any one or more measurements for use in methods according to some embodiments (e.g., on-line viscometers, pressure gauges, etc.). Thus, some embodiments may include a rock sample analysis system, which may be configured to perform some or all of the procedures according to various embodiments for substantially simultaneous determination of porosity and permeability of a rock sample, and characterization of formation fluid(s) from the sample. Some embodiments of a rock sample analysis system according to the present disclosure may include a rock sample chamber. The rock sample chamber may include an inlet for passing a cleaning fluid into the chamber and through the rock sample, and an outlet for the resulting effluent to flow through after exiting the rock sample. Each of the inlet and outlet may be in fluid communication with one or more conduits (e.g., pipes, tubes, capillaries or other means suitable for conducting a cleaning fluid into the chamber, through the rock sample, and out of the chamber), and each of the inlet and outlet may further include a valve for cutting off fluid communication with one or more of the conduit(s). The rock sample chamber may further include equipment configured to obtain one or more measurements for determining porosity and/or permeability based upon the cleaning fluid flow into the chamber and/or through the rock sample. For example, the chamber may include one or more pressure gauges for determining differential pressure at which the cleaning fluid flows through the rock sample. The chamber may include volumetric measurement means, such as a volume gauge, one or more dipsticks, and/or any device comprising one or more sensors for determining volume of cleaning fluid and/or volume of rock sample plus cleaning fluid within the rock sample chamber. Examples of the latter may include an acoustic, radar, rotary level indicator, bob-style sensor, or other sensor for determining fluid height in the chamber, and/or pressure gauge and temperature probe for determining pressure exerted by a gaseous cleaning fluid and temperature in the chamber. The rock sample chamber of some embodiments may further include a heat exchanger (e.g., a heating coil, steam jacket, or other means of providing heat to the chamber and thereby to the rock sample), and/or it may further include a steam input and output (e.g., for inputting and outputting, respectively, steam into and out of the chamber for heating and/or pressurizing the chamber and rock sample contained therein).

A conduit of the rock sample analysis system of some embodiments may include and/or be coupled to equipment (e.g., one or more devices) configured to measure one or more properties of either or both of the cleaning fluid and the effluent, wherein the one or more properties may include any property or properties sufficient to determine each of: a permeability value of the rock sample, a porosity value of the rock sample, and the composition of the portion of formation fluid(s) extracted in the effluent. Thus, for example, a conduit of some embodiments may include and/or be coupled to any one or more of a viscometer(s), densitometer(s), pressure gauge(s), gas chromatograph(s), liquid chromatograph(s), and mass spectrometer(s). Other equipment for measuring other properties may be included and/or coupled to conduits of some other embodiments. In addition, a conduit may be in fluid communication with a cleaning fluid pump configured to pump a cleaning fluid through the rock sample at differential pressure and/or flow rate sufficient to obtain measurements of the one or more properties such that the one or more properties may be used to determine a permeability value of the rock sample. A conduit may also or instead be in fluid communication with an effluent collection unit, and the effluent collection unit may in turn be coupled to, disposed on, and/or include a mass balance or other means of obtaining mass measurements of effluent collected in the effluent collection unit. The effluent collection unit of certain embodiments may also or instead include volume measurement equipment (such as any equipment suitable for volume measurement discussed previously in connection with the rock sample chamber).

Figure 1:
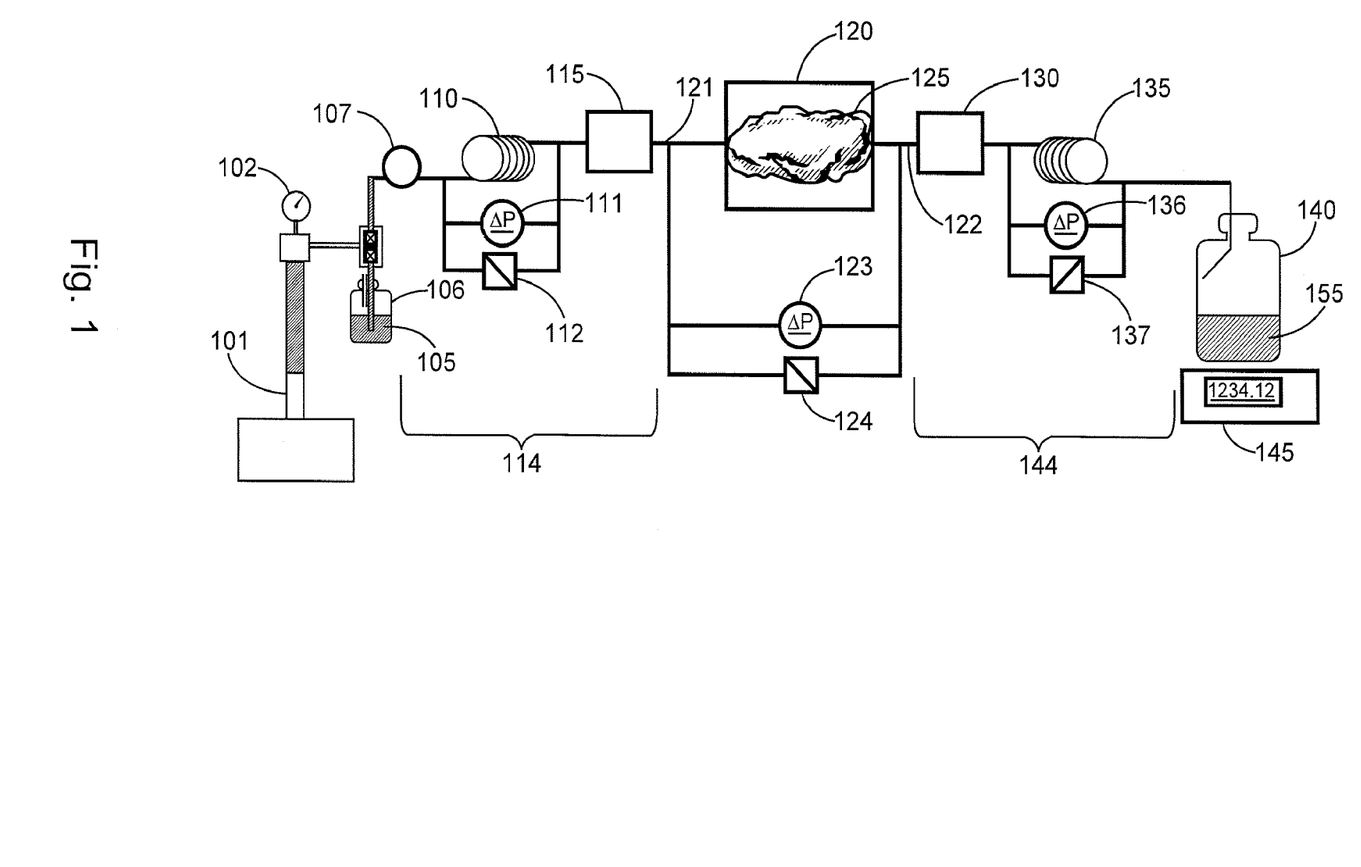
FIG. 1 is a diagram depicting an exemplary flow chart including equipment for carrying out methods according to aspects of the present disclosure.

An example process flow diagram including equipment according to a rock sample analysis system of some embodiments is shown in FIG. 1. Pump 101 with pressure gauge 102 pumps a cleaning fluid 105 from a reservoir 106. The cleaning fluid 105 passes through injection valve 107 to an inlet viscometer 110 (coupled via parallel piping to on-line pressure gauge 111 and bypass valve 112) and through an inlet densitometer 115 in succession, all via an inlet conduit 114 conveying the cleaning fluid from the cleaning fluid reservoir 106 through the just-described equipment and to a rock sample chamber 120. The viscometer 110 and densitometer 115 may be used to determine properties of the cleaning fluid (here, viscosity and density, respectively). As noted, the cleaning fluid 105 then passes into the rock sample chamber 120 where it passes through the core plug 125 (or other rock sample). The rock sample chamber, in some embodiments, may comprise a material such as graphite, hard plastic, or polytetrafluoroethylene (PTFE), commonly referred to by the brand name TEFLON®, as manufactured and sold by DuPont Co. Other materials may instead be used, but the chamber should be constructed of a material that is capable of withstanding sufficiently high pressures for driving a liquid solvent and/or a gas through the chamber without rupturing the chamber. The chamber should not react with suitable cleaning fluids for use in the systems and methods of the present disclosure. The chamber further comprises chamber inlet 121 and chamber outlet 122 for cleaning fluid flow into and out of the chamber, respectively. In some embodiments, either or both of the inlet 121 and/or outlet 122 may further include a valve (not shown in FIG. 1) for shutting off cleaning fluid flow, e.g., while soaking the rock sample 125 in the cleaning fluid 105. In addition, the chamber may include or coupled to parallel piping for each of chamber differential pressure gauge 123 and bypass valve 124.

The cleaning fluid extracts some portion of the formation fluid(s) from the core sample 125 and exits the rock sample chamber 120 at outlet 122 as effluent 155 (comprising the cleaning fluid 105 and extracted portion of formation fluid(s)). The effluent 155 passes through outlet densitometer 130 and outlet viscometer 135 to effluent collection unit 140, all via outlet conduit 144. The outlet viscometer 135 may include or be coupled to parallel piping for on-line differential pressure gauge 136 and bypass valve 137. Here, properties of the effluent may be determined (e.g., as shown by the configuration illustrated in FIG. 1, density and viscosity of the effluent). The effluent 155 is then collected in vessel 140, which may include or be situated upon a mass balance 145 or like device for determining mass of the collected effluent 155.

In certain embodiments, a rock analysis system may include or be communicatively coupled to a control system. In certain embodiments, a control system may be configured to and/or used to collect, process, and display data regarding rock sample analysis (either automatically via sensors at the well site or manually entered into the system), perform calculations using that data, as described above, and/or execute instructions to perform various functions at a well site. The control system may comprise an information handling system, such as a programmable logic controller or PLC, a suitably programmed computer, etc. Any suitable processing application software package may be used by the control system to process the data. In one embodiment, the software produces data that may be presented to the operation personnel in a variety of visual display presentations such as a display. In certain example systems, the measured value set of parameters (including rock sample permeability and porosity, and formation fluid(s) composition), the expected value set of parameters, or both may be displayed to the operator using the display. For example, the measured-value set of parameters may be juxtaposed to the expected-value set of parameters using the display, allowing the user to manually identify, characterize, or locate a downhole condition (such as porosity, permeability, or formation fluid(s) composition). The sets may be presented to the user in a graphical format (e.g., a chart) or in a textual format (e.g., a table of values). In another example system, the display may show warnings or other information to the operator when the central monitoring system detects a downhole condition. Suitable control systems and interfaces for use in the methods and systems of the present disclosure may comprise SENTRY™ and INSITE™ provided by Halliburton Energy Services, Inc. Any suitable control system or interface may be used in keeping with the principles of this disclosure.

In certain embodiments, the control system may be communicatively coupled to an external communications interface. The external communications interface may permit the data from the control system to be remotely accessible (i.e., from a location other than the well site) by any remote information handling system communicatively coupled to the external communications interface via, for example, a satellite, a modem or wireless connections. In one embodiment, the external communications interface may include a router.

In accordance with certain embodiments of the present disclosure, once feeds from one or more sensors are obtained, they may be combined and used to identify various metrics. For instance, if there is data that deviates from normal expectancy at the rig site, the combined system may show another reading of the data from another sensor that may help identify the type of deviation. As would be appreciated by those of ordinary skill in the art, with the benefit of this disclosure, a control system may also collect data from multiple rig sites and wells to perform quality checks across a plurality of rigs.

As would be appreciated by those of ordinary skill in the art, with the benefit of this disclosure, one or more information handling systems may be used to implement the methods disclosed herein. In certain embodiments, the different information handling systems may be communicatively coupled through a wired or wireless system to facilitate data transmission between the different subsystems. Moreover, each information handling system may include computer readable media to store data generated by the subsystem as well as preset job performance requirements and standards. The computer readable media may include instructions that, when executed, perform or cause the performance of one or more methods according to the present disclosure.

Furthermore, one or more rock sample analysis systems configured to pass a cleaning fluid through a rock sample may be positioned on-site at a rig site. In some embodiments, one or more rock sample analysis systems may be incorporated into or coupled to one or more components of a drilling system.

The exemplary rock sample analysis methods and systems disclosed herein may directly or indirectly affect one or more components or pieces of equipment associated with the drilling of a well through a subterranean formation. For example, and with reference to FIG. 2, the disclosed well evaluation pills, methods, and systems may directly or indirectly affect one or more components or pieces of equipment associated with an exemplary well bore drilling assembly 200, according to one or more embodiments. It should be noted that while FIG. 2 generally depicts a land-based drilling assembly, those skilled in the art will readily recognize that the principles described herein are equally applicable to subsea drilling operations that employ floating or sea-based platforms and rigs, without departing from the scope of the disclosure.

Figure 2:
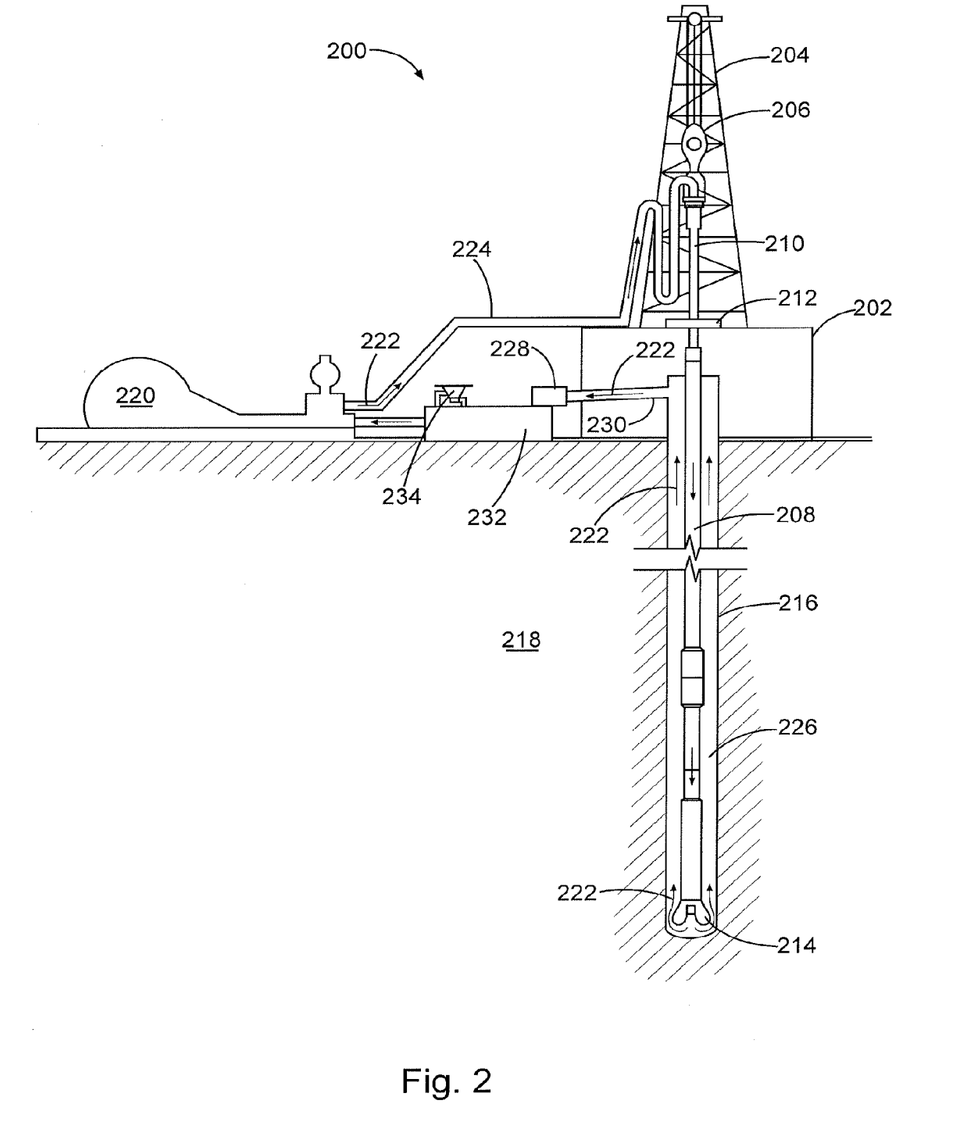
FIG. 2 is a stylistic representation of an example of a well bore drilling assembly that may be used in accordance with certain embodiments of the present disclosure.

As illustrated, the drilling assembly 200 may include a drilling platform 202 that supports a derrick 204 having a traveling block 206 for raising and lowering a drill string 208. The drill string 208 may include, but is not limited to, drill pipe and coiled tubing, as generally known to those skilled in the art. A kelly 210 supports the drill string 208 as it is lowered through a rotary table 212. A drill bit 214 is attached to the distal end of the drill string 208 and is driven either by a downhole motor and/or via rotation of the drill string 208 from the well surface. As the bit 214 rotates, it creates a borehole 216 that penetrates various subterranean formations 218.

A pump 220 (e.g., a mud pump) circulates drilling fluid 222 through a feed pipe 224 and to the kelly 210, which conveys the drilling fluid 222 downhole through the interior of the drill string 208 and through one or more orifices in the drill bit 214. While downhole, the drilling fluid 222 may come into contact with one or more rock samples (e.g., cuttings resulting from the boring of the drill bit 214 into the one or more subterranean formations 218). The drilling fluid 222, in some instances carrying cuttings or other rock samples (not shown), is then circulated back to the surface via an annulus 226 defined between the drill string 208 and the walls of the borehole 216. At the surface, the recirculated or spent drilling fluid 222 exits the annulus 226 and may be conveyed to one or more fluid processing unit(s) 228 via an interconnecting flow line 230. At fluid processing unit(s) 228, the one or more rock samples may be extracted or otherwise separated from the drilling fluid 222. After passing through the fluid processing unit(s) 228, a "cleaned" drilling fluid 222 is deposited into a nearby retention pit 232 (i.e., a mud pit). While illustrated as being arranged at the outlet of the well bore 216 via the annulus 226, those skilled in the art will readily appreciate that the fluid processing unit(s) 228 may be arranged at any other location in the drilling assembly 200 to facilitate its proper function, without departing from the scope of the scope of the disclosure.

One or more additives may be added to the drilling fluid 222 via a mixing hopper 234 communicably coupled to or otherwise in fluid communication with a retention pit 232. The mixing hopper 234 may include, but is not limited to, mixers and related mixing equipment known to those skilled in the art. In other embodiments, however, the additives may be added to the drilling fluid 222 at any other location in the drilling assembly 200. In at least one embodiment, for example, there could be more than one retention pit 232, such as multiple retention pits 232 in series. Moreover, the retention pit 232 may be representative of one or more fluid storage facilities and/or units where additives may be stored, reconditioned, and/or regulated until added to the drilling fluid 222 and/or introduced into the well bore.

As mentioned above, the disclosed rock sample analysis methods and systems may directly or indirectly affect the components and equipment of the drilling assembly 200. For example, the disclosed rock analysis methods and systems may directly or indirectly affect the fluid processing unit(s) 228 which may include, but is not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, any fluid reclamation equipment, or the like. The fluid processing unit(s) 228 may further include one or more sensors, gauges, pumps, compressors, and the like used store, monitor, regulate, and/or recondition the well evaluation pill and/or other fluids. Specifically, the disclosed rock analysis methods and systems may include obtaining a rock sample (e.g., a core wall sample, a cutting, or the like). In some instances, a rock sample may be obtained from the drilling fluid from and/or using one or more fluid processing unit(s) 228. Obtaining a rock sample may include separating one or more rock samples from the drilling fluid 222, and it may further include performing a lag time measurement or other means of associating a downhole location with that rock sample, as previously discussed herein. Such measurement or other means may be in whole or in part automated (e.g., by computation or other determination carried out by an information handling system communicatively coupled to the fluid processing unit(s) 228 and/or the pump 220 and/or the traveling block 206). The fluid processing unit(s) may be in fluid communication with a rock sample analysis system according to some embodiments; for example, a rock sample or samples may be delivered from one or more fluid processing unit(s) to a rock sample chamber of one or each of multiple rock sample analysis system(s). In some embodiments, the fluid processing unit 228 may include one or more rock sample analysis system(s) according to the present disclosure.

The disclosed rock sample analysis methods and systems may directly or indirectly affect the pump 220, which representatively includes any conduits, pipelines, trucks, tubulars, and/or pipes used to fluidically convey the fluids and additives downhole, any pumps, compressors, or motors (e.g., topside or downhole) used to drive the fluids into motion, any valves or related joints used to regulate the pressure or flow rate of the fluids and additives, and any sensors (i.e., pressure, temperature, flow rate, etc.), gauges, and/or combinations thereof, and the like. The disclosed rock sample analysis methods and systems may also directly or indirectly affect the mixing hopper 134 and the retention pit 132 and their assorted variations.

The disclosed rock sample analysis methods and systems may also directly or indirectly affect the various downhole equipment and tools that may come into contact with the fluids and/or rock samples such as, but not limited to, the drill string 208, any floats, drill collars, mud motors, downhole motors and/or pumps associated with the drill string 208, and any MWD/LWD tools and related telemetry equipment, sensors or distributed sensors associated with the drill string 208. The disclosed rock sample analysis methods and systems may also directly or indirectly affect any downhole heat exchangers, valves and corresponding actuation devices, tool seals, packers and other well bore isolation devices or components, and the like associated with the well bore 216. The disclosed rock sample analysis methods and systems may also directly or indirectly affect the drill bit 214, which may include, but is not limited to, roller cone bits, PDC bits, natural diamond bits, any hole openers, reamers, coring bits, etc.

While not specifically illustrated herein, the disclosed rock sample analysis methods and systems may also directly or indirectly affect any transport or delivery equipment used to convey the fluids and additives to the drilling assembly 200 such as, for example, any transport vessels, conduits, pipelines, trucks, tubulars, and/or pipes used to fluidically move the fluids and/or rock samples from one location to another, any pumps, compressors, or motors used to drive the fluids and/or rock samples into motion, any valves or related joints used to regulate the pressure or flow rate of the fluids and/or fluids including rock samples, and any sensors (i.e., pressure and temperature), gauges, and/or combinations thereof, and the like.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer or tablet device, a cellular telephone, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

The terms "couple" or "couples," as used herein are intended to mean either an indirect or a direct connection. Thus, if a first device couples to a second device, that connection may be through a direct connection, or through an indirect electrical connection via other devices and connections. The term "communicatively coupled" as used herein is intended to mean coupling of components in a way to permit communication of information therebetween. Two components may be communicatively coupled through a wired or wireless communication network, including but not limited to Ethernet, LAN, fiber optics, radio, microwaves, satellite, and the like. Operation and use of such communication networks is well known to those of ordinary skill in the art and will, therefore, not be discussed in detail herein.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

What is claimed is:

1. A method comprising:
   passing a cleaning fluid at a flow rate through a rock sample at a differential pressure, so as to extract at least a portion of one or more naturally occurring formation fluids from the rock sample, wherein the one or more naturally occurring formation fluids comprise one or more fluids that reside in a subterranean formation from which the rock sample was taken;
   collecting an effluent comprising the cleaning fluid and the portion of the one or more naturally occurring formation fluids;
   determining one or more properties of the cleaning fluid;
   determining the composition of the effluent;
   based at least in part on (i) the one or more properties of the cleaning fluid, and (ii) the composition of the effluent, performing a calculation analytically to determine one or more properties of the effluent by performing an extrapolation using a weighting factor equal to an inverse of a mass fraction of the cleaning fluid, wherein the one or more properties of the effluent are selected from the group consisting of: a viscosity of the effluent, a density of the effluent, and a mass of the effluent;

determining a volume of the rock sample and a volume of the portion of the one or more naturally occurring formation fluids;

based at least in part on one or more of the properties of the effluent, determining one or more properties of the portion of the one or more naturally occurring formation fluids;

based at least in part on one or more of (i) one or more properties of the effluent, (ii) the flow rate of the cleaning fluid, and (iii) the differential pressure of the cleaning fluid, determining a permeability value of the rock sample; and based at least in part on one or more of (i) the volume of the portion of the one or more naturally occurring formation fluids and (ii) the volume of the rock sample, determining a porosity value of the rock sample.

2. The method of claim 1 wherein the one or more properties of the cleaning fluid comprise one or more of density, composition, and viscosity; wherein the one or more properties of the effluent comprise one or more of density, composition, and viscosity; and wherein the one or more properties of the portion of the one or more naturally occurring formation fluids comprises composition.

3. The method of claim 1 wherein the cleaning fluid is hydrophobic, and wherein the cleaning fluid is passed through the rock sample at the differential pressure such that the extracted portion of the one or more naturally occurring formation fluids comprises a hydrocarbon fraction and formation water.

4. The method of claim 1 further comprising measuring one of the flow rate and the differential pressure, wherein the other of flow rate and differential pressure is substantially constant while the cleaning fluid is passed through the rock sample.

5. The method of claim 1 wherein the cleaning fluid is hydrophobic, and wherein a permeability value is an effective oil phase permeability.

6. The method of claim 5 further comprising obtaining the rock sample from a subterranean formation and determining a second permeability value based at least in part on one or more properties of the subterranean formation from which the rock sample is obtained, wherein the second permeability value is an absolute permeability of the rock sample.

7. The method of claim 1 wherein the cleaning fluid is hydrophilic, and wherein a first permeability value is an effective water phase permeability.

8. The method of claim 7 further comprising:

obtaining the rock sample from a subterranean formation;

determining a second permeability value based at least in part on one or more properties of the subterranean formation from which the rock sample is obtained, wherein the second permeability value is an absolute permeability of the rock sample; and determining an effective oil phase permeability of the rock sample based at least in part on the determined permeability value, the determined second permeability value, and the one or more properties of the portion of the one or more naturally occurring formation fluids.

9. The method of claim 1 further comprising:

soaking the rock sample in additional cleaning fluid so as to extract an additional portion of the one or more naturally occurring formation fluids from the rock sample;

collecting a second effluent comprising the additional cleaning fluid and the extracted additional portion of the one or more naturally occurring formation fluids; and determining the volume of the second portion of the one or more naturally occurring formation fluids;

wherein determining the porosity value of the rock sample is based further at least in part on the determined volume of the second portion of the one or more naturally occurring formation fluids.

10. The method of claim 1, wherein the rock sample comprises one or more drill cuttings.

11. A method comprising:

passing a first cleaning fluid at a first flow rate through a rock sample at a first differential pressure, so as to extract at least a first portion of one or more naturally occurring formation fluids from the rock sample, wherein the one or more naturally occurring formation fluids comprise one or more fluids that reside in a subterranean formation from which the rock sample was taken;

collecting a first effluent comprising the first cleaning fluid and the first portion of the one or more naturally occurring formation fluids;

passing a second cleaning fluid at a second flow rate through the rock sample at a second differential pressure, so as to extract at least a second portion of the one or more naturally occurring formation fluids from the rock sample;

collecting a second effluent comprising the second cleaning fluid and the second portion of the one or more naturally occurring formation fluids;

determining one or more properties of the first cleaning fluid;

determining the composition of the first effluent;

based at least in part on (i) the one or more properties of the first cleaning fluid and (ii) the composition of the first effluent, performing a calculation analytically to determine one or more properties of the first effluent by performing an extrapolation using a weighting factor equal to an inverse of a mass fraction of the first cleaning fluid, wherein the one or more properties of the first effluent are selected from the group consisting of: a viscosity of the first effluent, a density of the effluent, and a mass of the first effluent;

determining one or more properties of the second effluent;

determining a volume of the rock sample, a volume of the first portion of the one or more naturally occurring formation fluids, and a volume of the second portion of the one or more naturally occurring formation fluids;

based at least in part on one or more of the properties of the first effluent, determining one or more properties of the first portion of the one or more naturally occurring formation fluids;

based at least in part on one or more of the properties of the second effluent, determining one or more properties of the second portion of the one or more naturally occurring formation fluids;

based at least in part on one or more of (i) one or more of the properties of the first effluent, (ii) the first flow rate of the first cleaning fluid, and (iii) the first differential pressure of the first cleaning fluid, determining a first permeability value of the rock sample; and based at least in part on one or more of (i) the volume of the first portion of the one or more naturally occurring formation fluids, (ii) the volume of the second portion of the one or more naturally occurring formation fluids, and (ii) the volume of the rock sample, determining a porosity value of the rock sample.

12. The method of claim 11 further comprising: based at least in part on one or more of (i) one or more of the properties of the second effluent, (ii) the second flow rate of the second cleaning fluid, and (iii) the second differential pressure of the second cleaning fluid, determining a second permeability value of the rock sample.

13. The method of claim 12 further comprising: based at least in part on (i) the first and second permeability values, (ii) one or more of the properties of the first effluent, and (iii) one or more of the properties of the second effluent, determining a profile of permeability versus composition of the one or more naturally occurring formation fluids.

14. The method of claim 11 further comprising:
soaking the rock sample in additional first cleaning fluid so as to extract a first additional portion of the one or more naturally occurring formation fluids;
collecting a first additional effluent comprising the additional first cleaning fluid and the first additional portion of the one or more naturally occurring formation fluids;
soaking the rock sample in additional second cleaning fluid so as to extract a second additional portion of the one or more naturally occurring formation fluids;
collecting a second additional effluent comprising the additional second cleaning fluid and the second additional portion of the one or more naturally occurring formation fluids;
determining the volume of the first additional portion of the one or more naturally occurring formation fluids; and
determining the volume of the second additional portion of the one or more naturally occurring formation fluids.

15. The method of claim 11, wherein the rock sample comprises one or more drill cuttings.

16. A system comprising:
a fluid processing unit that removes one or more rock samples from a drilling fluid that has been circulated in a well bore penetrating at least a portion of a subterranean formation; and
a rock sample analysis system configured to pass a cleaning fluid through one of the rock samples at a flow rate and a differential pressure so that the cleaning fluid extracts at least a portion of one or more naturally occurring formation fluids from the rock sample in an effluent comprising the cleaning fluid and the portion of the one or more naturally occurring formation fluids, the rock sample analysis system comprising equipment configured to allow a calculation to be analytically performed by performing an extrapolation using a weighting factor equal to an inverse of a mass fraction of the cleaning fluid to determine a viscosity of the effluent, a density of the effluent, a mass of the effluent, and obtain one or more rock sample analysis measurements selected from the group consisting of: the flow rate of the cleaning fluid, the differential pressure of the cleaning fluid, one or more properties of the cleaning fluid, and wherein the one or more naturally occurring formation fluids comprise one or more fluids that reside in a subterranean formation from which the rock sample was taken.

17. The system of claim 16 further comprising an information handling system communicatively coupled to the rock sample analysis system so as to receive the one or more rock sample analysis measurements, the information handling system comprising:
one or more processing resources, and
computer readable media including instructions that, when executed, cause the one or more processing resources to: (i) determine, based at least in part on one or more of the one or more rock sample analysis measurements, a permeability value of the rock sample; (ii) determine, based at least in part on one or more of the rock sample analysis measurements, a porosity value of the rock sample; and (iii) determine, based at least in part on any one or more of the one or more rock sample analysis measurements, the composition of the portion of the one or more naturally occurring formation fluids extracted from the rock sample.

18. The system of claim 16, wherein the one or more rock samples comprises one or more drill cuttings.

* * * * *